(12) United States Patent
Hengst et al.

(10) Patent No.: US 11,440,833 B2
(45) Date of Patent: Sep. 13, 2022

(54) FLUORESCENT GLASS CERAMICS AND GLASSES WITH CERIUM AND TIN CONTENT

(71) Applicant: Ivoclar Vivadent AG, Schaan (LI)

(72) Inventors: Ronny Hengst, Brand-Erbisdorf (DE); Marc Dittmer, Feldkirch (AT)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 16/783,750

(22) Filed: Feb. 6, 2020

(65) Prior Publication Data

US 2020/0262738 A1 Aug. 20, 2020

(30) Foreign Application Priority Data

Feb. 14, 2019 (EP) .................................... 19157303

(51) Int. Cl.
   *C03C 3/085* (2006.01)
   *C03C 10/00* (2006.01)

(52) U.S. Cl.
   CPC .......... *C03C 3/085* (2013.01); *C03C 10/0018* (2013.01); *C03C 2205/06* (2013.01)

(58) Field of Classification Search
   CPC .. C03C 3/085; C03C 10/0018; C03C 2205/06
   See application file for complete search history.

(56) References Cited

U.S. PATENT DOCUMENTS

| | | | |
|---|---|---|---|
| 5,432,130 A | 7/1995 | Rheinberger et al. | |
| 5,618,763 A | 4/1997 | Frank et al. | |
| 5,698,019 A | 12/1997 | Frank et al. | |
| 5,925,180 A | 7/1999 | Frank et al. | |
| 6,455,451 B1 | 9/2002 | Brodkin et al. | |
| 7,667,791 B2 | 2/2010 | Shiratori et al. | |
| 7,977,262 B2 * | 7/2011 | Motoya | C03C 4/085 501/64 |
| 8,047,021 B2 | 11/2011 | Schweiger et al. | |
| 8,263,508 B2 | 9/2012 | Bolle et al. | |
| 9,277,971 B2 | 3/2016 | Castillo | |
| 9,321,674 B2 | 4/2016 | Ritzberger et al. | |
| 9,402,699 B2 | 8/2016 | Ritzberger et al. | |
| 9,403,714 B2 | 8/2016 | Ritzberger et al. | |
| 9,688,567 B2 | 6/2017 | Rampf et al. | |
| 9,695,082 B2 | 7/2017 | Ritzberger et al. | |
| 9,757,311 B2 | 9/2017 | Rampf et al. | |
| 9,764,982 B2 | 9/2017 | Ritzberger et al. | |
| 9,776,912 B2 | 10/2017 | Ritzberger et al. | |
| 9,878,939 B2 | 1/2018 | Ritzberger et al. | |
| 10,131,569 B2 | 11/2018 | Krolikowski et al. | |
| 10,227,255 B2 | 3/2019 | Ritzberger et al. | |
| 10,376,343 B2 | 8/2019 | Ritzberger et al. | |
| 10,377,661 B2 | 8/2019 | Rampf et al. | |
| 10,414,688 B2 | 9/2019 | Rampf et al. | |
| 10,457,589 B2 | 10/2019 | Rampf et al. | |
| 10,501,366 B2 | 12/2019 | Ritzberger et al. | |
| 2010/0083706 A1 | 4/2010 | Castillo | |
| 2018/0244563 A1 | 8/2018 | Dittmer et al. | |
| 2019/0365515 A1 | 12/2019 | Dittmer et al. | |

FOREIGN PATENT DOCUMENTS

| | | | |
|---|---|---|---|
| DE | 19647739 A1 | 3/1998 | |
| DE | 19725552 A1 | 12/1998 | |
| DE | 10031431 A1 | 1/2002 | |
| EP | 0827941 A1 | 3/1998 | |
| EP | 0916625 A1 * | 5/1999 | ............. A61K 6/807 |
| EP | 0916625 A1 | 5/1999 | |
| EP | 1688398 A1 | 8/2006 | |
| EP | 3135641 A1 * | 3/2017 | ............. C03C 3/087 |

OTHER PUBLICATIONS

Tin_II_oxide_-_Wikipedia_the_free_encyclopedia.pdf; accessed from https://web.archive.org/web/20141225205114/https://en.wikipedia.org/wiki/Tin(II)_oxide (Year: 2014).*
EP-3135641-A1 translation (Year: 2017).*
EP-0916625-A1 translation (Year: 1999).*
Rukmani, S. J. et al., "Effects of V and Mn Colorants on the Crystallization Behavior and Optical Properties of Ce-Doped Li-Disilicate Glass-Ceramics," J. Am. Ceram. Soc., 90 [3], pp. 706-711, The American Ceramic Society, 2007.
Buchalla, W., "Comparative Fluorescence Spectroscopy Shows Differences in Noncavitated Enamel Lesions," Caries Research, 39, pp. 150-156, S. Karger AG, Basel, 2005.

* cited by examiner

*Primary Examiner* — Karl E Group
*Assistant Examiner* — Cameron K Miller
(74) *Attorney, Agent, or Firm* — Ann M. Knab; Thad McMurray

(57) ABSTRACT

The invention relates to glass ceramics and glasses with cerium and tin content, which comprise the following components:

| Component | wt.-% |
|---|---|
| $SiO_2$ | 42.0 to 80.0 |
| $Al_2O_3$ | 0.1 to 42.0 |
| Cerium, calculated as $CeO_2$ | 0.5 to 10.0 |
| Tin, calculated as SnO | 0.1 to 4.0 | and which are suitable in particular for the preparation of dental restorations, the fluorescence properties of which largely correspond to those of natural teeth.

18 Claims, No Drawings

FLUORESCENT GLASS CERAMICS AND GLASSES WITH CERIUM AND TIN CONTENT

CROSS-REFERENCE TO RELATED APPLICATIONS

This application claims priority to European patent application No. 19157303.9 filed on Feb. 14, 2019, the disclosure of which is incorporated herein by reference in its entirety.

FIELD OF INVENTION

The present invention relates to glass ceramics and glasses which comprise cerium and tin and are suitable in particular for the production of dental restorations, the fluorescence properties of which largely correspond to those of natural teeth. The invention also relates to a process for the preparation of the glass ceramics and glasses according to the invention as well as their use as dental material and in particular for the preparation of dental restorations.

BACKGROUND

Glass ceramics are used in dentistry because of their good mechanical and optical properties in particular for the production of dental crowns and small bridges.

EP 0 916 625 A1 describes lithium disilicate glass ceramics which contain lithium disilicate as main crystal phase and, because of their high translucence and very good mechanical properties, are used in particular in the dental field, and primarily for the production of crowns and bridges. In order to adapt the colour of the glass ceramic products to the colour of natural tooth material, the glass ceramics can have colour and fluorescence components which are preferably selected from the group consisting of $CeO_2$, $V_2O_5$, $Fe_2O_3$, $MnO_2$, $TiO_2$, $Y_2O_3$, $Er_2O_3$, $Tb_4O_7$, $Eu_2O_3$, $Yb_2O_3$, $Gd_2O_3$, $Nd_2O_3$, $Pr_2O_3$, $Dy_2O_3$, $Ag_2O$, $SnO_2$ and $Ta_2O_5$.

WO 2015/173394 A1 and corresponding U.S. Ser. No. 10/377,661, which is hereby incorporated by reference in its entirety, describes glass ceramics which have $SiO_2$ as main crystal phase and are likewise suitable for the production of dental restorations. These glass ceramics can contain, in particular, oxides of Sc, Mn, Fe, Co, Pr, Nd, Tb, Er, Dy, Gd, Eu and Yb as colorants or fluorescent agents.

It is known from W. Buchalla, "Comparative Fluorescence Spectroscopy Shows Differences in Non-Cavitated Enamel Lesions", Caries Res. 2005, 39, 150-156, that, under ultraviolet light, natural teeth exhibit a bluish-white fluorescence with wavelengths in the range of from 400 to 650 nm.

Rukmani et al., J. Am. Ceram. Soc. 2007, 90, 706-711, describe the influence of V and Mn colorants on the crystallization behaviour and the optical properties of Ce-doped lithium disilicate glass ceramics. For the production of the glass ceramics, a mixture of the starting materials $SiO_2$, $ZrO_2$, $Li_2CO_3$, $K_2CO_3$, $MgCO_3$ and $Al(PO_3)_3$ with $CeO_2$, $V_2O_5$ and $MnO_2$ is produced, the mixture is melted in platinum crucibles at 1500° C., cooled and then subjected to several heat treatments in a tube furnace with an air supply.

However, it has been shown that the glasses and glass ceramics known from the state of the art have unsatisfactory fluorescence properties and, in particular under UV light, cannot adequately imitate the fluorescence properties of natural tooth material. Dental restorations produced from such glass ceramics are thereby recognizable as restorations, in particular under the influence of UV light, or are perceived as missing teeth or defects.

Processes for the production of glasses and glass ceramics with improved fluorescence properties have likewise been described.

Thus WO 2015/173230 A1 and corresponding U.S. Ser. No. 10/131,569, which is hereby incorporated by reference in its entirety, describe a method for the production of a lithium silicate glass or a lithium silicate glass ceramic, in which a melt of a starting glass which contains cerium ions is exposed to reducing conditions. $Ce^{4+}$ ions contained in the starting glass shall thereby completely or partially be reduced to $Ce^{3+}$ ions which, because of 5d→4f transitions, exhibit a fluorescence in the wavelength range from 320 to 500 nm. A corresponding method for the production of a glass ceramic with $SiO_2$ as main crystal phase or of a glass which contains nuclei for the crystallization of $SiO_2$, is known from WO 2017/080853 A1 and corresponding U.S. Ser. No. 10/414,688, which is hereby incorporated by reference in its entirety.

However, a disadvantage of the known processes is that the ratio of $Ce^{3+}$ ions to $Ce^{4+}$ ions can only be partially controlled. Moreover, in the case of the glasses and glass ceramics produced in this way, this ratio can be shifted in favour of $Ce^{4+}$ ions through heat treatments under oxidizing conditions, for example during sintering, whereby the fluorescence properties can be significantly impaired.

SUMMARY

The object of the invention is to provide glass ceramics and glasses which exhibit a fluorescence that is comparable to natural tooth material and largely insensitive with respect to heat treatments and oxidizing conditions, and which are thus suitable in particular for the production of dental restorations which not only have good mechanical properties, but can also largely imitate the fluorescence properties of natural tooth material at excitation wavelengths throughout the entire relevant UV range. In particular, the glass ceramics and glasses should also be suitable as blending components for setting the fluorescence properties of other glasses or glass ceramics.

DETAILED DESCRIPTION

This object is achieved according to the invention by a glass or a glass ceramic with cerium and tin content, which comprise the following components:

| Component | wt.-% |
|---|---|
| $SiO_2$ | 42.0 to 80.0 |
| $Al_2O_3$ | 0.1 to 42.0 |
| Cerium, calculated as $CeO_2$ | 0.5 to 10.0 |
| Tin, calculated as SnO | 0.1 to 4.0. |

It has surprisingly been shown that the glass according to the invention and the glass ceramic according to the invention exhibit improved fluorescence properties compared with the state of the art, in particular under the action of UV light, which can be set accurately and reproducibly and are largely stable towards heat treatments and oxidizing conditions.

Without being limited to a specific theory, it is assumed that an equilibrium between $Ce^{3+}/Ce^{4+}$ and $Sn^{2+}/Sn^{4+}$ is formed in the glasses and glass ceramics according to the invention. The ratio of $Ce^{3+}$ ions to $Ce^{4+}$ ions is thereby stabilized and an undesired shift of this ratio towards $Ce^{4+}$ ions e.g. in the case of heat treatments in particular under oxidizing conditions is largely prevented. Because of $5d \rightarrow 4f$ transitions, the $Ce^3$ ions exhibit a fluorescence in the wavelength range of from 320 to 500 nm which is particularly suitable for imitating the fluorescence properties of natural tooth material. In addition, $Ce^{4+}$ ions bring about a yellow coloration of the glasses and glass ceramics. A particularly good imitation of the fluorescence and colour properties of natural tooth material is thus made possible.

According to the invention, it is preferred that the glass and the glass ceramic comprise 46.0 to 77.0, in particular 59.0 to 76.0, preferably 64.0 to 75.0 and particularly preferably 70.0 to 74.0 wt.-% $SiO_2$.

It is further preferred that the glass and the glass ceramic comprise 0.3 to 39.0, in particular 0.5 to 30.0, preferably 1.0 to 20.0, particularly preferably 1.5 to 10.0 and most preferably 2.0 to 6.0 wt.-% $Al_2O_3$.

The glass and the glass ceramic preferably comprise 0.7 to 7.5, in particular 1.0 to 7.0, preferably 1.5 to 5.0, and particularly preferably 2.0 to 4.0 wt.-% cerium, calculated as $CeO_2$.

It is further preferred that the glass and the glass ceramic comprise 0.2 to 3.0, in particular 0.3 to 2.0 and preferably 0.4 to 1.0 wt.-% tin, calculated as SnO.

In addition, it is preferred that the molar ratio of cerium, calculated as $CeO_2$, to tin, calculated as SnO, lies in the range of from 10:1 to 1:5, in particular 5:1 to 1:2.5, preferably 3:1 to 1:1.5 and particularly preferably 2:1 to 1:1.

In a particular embodiment, the glass and the glass ceramic further comprise terbium. The glass and the glass ceramic preferably comprise 0 to 2.0, in particular 0.05 to 1.5, preferably 0.1 to 1.0, and particularly preferably 0.3 to 0.7 wt.-% terbium, calculated as $Tb_4O_7$. It has surprisingly been shown that according to the invention, through the combination of cerium ions and terbium ions, glasses and glass ceramics can be obtained, the fluorescence and colour properties of which can imitate those of natural tooth material particularly well. It is particularly surprising that, in the case of the glasses and glass ceramics according to the invention, the fluorescence induced by the cerium ions is also largely maintained in the presence of terbium ions, although in the state of the art a reduction or even extinguishing of the fluorescence induced by cerium ions was observed in the presence of d elements.

It is further preferred that the glass and the glass ceramic comprise 0 to 18.0, in particular 1.0 to 17.0, preferably 3.0 to 16.0, and particularly preferably 7.5 to 10.0 wt.-% $Li_2O$. $Li_2O$ serves in particular to improve the meltability of the starting glasses.

It is also preferred that the glass and the glass ceramic comprise further alkali metal oxide $Me^I_2O$ in an amount of 0 to 13.0, in particular 1.0 to 7.0 and preferably 3.0 to 5.0 wt.-%. The term "further alkali metal oxide $Me^I_2O$" denotes alkali metal oxide with the exception of $Li_2O$, wherein this $Me^I_2O$ is selected in particular from $Na_2O$, $K_2O$, $Rb_2O$ and/or $Cs_2O$, is preferably selected from $Na_2O$ and/or $K_2O$ and particularly preferably is $K_2O$. Particularly preferably, the glass and the glass ceramic comprise at least one and in particular all of the following further alkali metal oxides $Me^I O_2$ in the specified amounts:

| Component | wt.-% |
|---|---|
| $Na_2O$ | 0 to 8.0 |
| $K_2O$ | 0 to 5.0 |
| $Rb_2O$ | 0 to 7.0 |
| $Cs_2O$ | 0 to 13.0 |

Furthermore, it is preferred that the glass and the glass ceramic comprise 0 to 22.0, in particular 1.0 to 16.0, preferably 2.0 to 10.0 and particularly preferably 3.0 to 6.0 wt.-% further oxide of divalent elements $Me^{II}O$. The term "further oxide of divalent elements $Me^{II}O$" denotes divalent oxides with the exception of BaO and SnO, wherein this $Me^{II}O$ is selected in particular from MgO, CaO, SrO and/or ZnO. Particularly preferably, the glass and the glass ceramic comprise at least one and in particular all of the following oxides of divalent elements $Me^{II}O$ in the specified amounts:

| Component | wt.-% |
|---|---|
| MgO | 0 to 13.0 |
| CaO | 0 to 4.0 |
| SrO | 0 to 3.0 |
| ZnO | 0 to 4.0 |

It is furthermore preferred that the glass and the glass ceramic comprise 0 to 10.0, in particular 0 to 5.0 and preferably 0 to 1.0 wt.-% BaO, and most preferably are substantially free from BaO.

A glass and a glass ceramic are further preferred which comprise 0 to 10.0, in particular 0.5 to 4.0 and preferably 1.0 to 2.5 wt.-% further oxide of trivalent elements $Me^{III}_2O_3$. The term "further oxide of trivalent elements $Me^{III}_2O_3$" denotes trivalent oxides with the exception of $Al_2O_3$ and $Ce_2O_3$, wherein this $M^{III}_2O_3$ is selected in particular from $B_2O_3$, $Y_2O_3$, $La_2O_3$, $Ga_2O_3$ and/or $In_2O_3$ and is preferably selected from $B_2O_3$, $Y_2O_3$ and/or $La_2O_3$. Particularly preferably, the glass and the glass ceramic comprise at least one and in particular all of the following further oxides of trivalent elements $M^{III}_2O_3$ in the specified amounts:

| Component | wt.-% |
|---|---|
| $B_2O_3$ | 0 to 5.0 |
| $Y_2O_3$ | 0 to 3.0 |
| $La_2O_3$ | 0 to 2.0 |
| $Ga_2O_3$ | 0 to 2.0 |
| $In_2O_3$ | 0 to 1.0 |

Furthermore, the glass and the glass ceramic can comprise further oxide of tetravalent elements $Me^{IV}O_2$ in an amount of from 0 to 10.0, in particular 0.5 to 4.0 and preferably 1.0 to 2.5 wt.-%. The term "further oxide of tetravalent elements $Me^{IV}O2$" denotes tetravalent oxides with the exception of $SiO_2$, $CeO_2$, $SnO_2$ and $TiO_2$, wherein this $Me^{IV}O_2$ is selected in particular from $ZrO_2$ and/or $GeO_2$. Particularly preferably, the glass and the glass ceramic comprise at least one and in particular all of the following further oxides of tetravalent elements $Me^{IV}O_2$ in the specified amounts:

| Component | wt.-% |
|---|---|
| $ZrO_2$ | 0 to 8.0 |
| $GeO_2$ | 0 to 5.0 |

It is furthermore preferred that the glass and the glass ceramic comprise 0 to 5.0, in particular 0 to 2.5 and preferably 0 to 1.0 wt.-% $TiO_2$, and most preferably are substantially free from $TiO_2$.

In a preferred embodiment, the glass and the glass ceramic further comprise oxide of pentavalent elements $Me^V{}_2O_5$ in an amount of from 0 to 8.0, in particular 1.0 to 6.0, preferably 2.0 to 5.0 and particularly preferably 3.0 to 4.0 wt.-%, wherein this $Me^V{}_2O_5$ is selected in particular from $P_2O_5$, $V_2O_5$, $Ta_2O_5$ and/or $Nb_2O_5$, is preferably selected from $P_2O_5$ and/or $Ta_2O_5$ and particularly preferably is $P_2O_5$. $P_2O_5$ can in particular function as nucleating agent. However, the presence of a nucleating agent is not absolutely necessary according to the invention. Particularly preferably, the glass and the glass ceramic comprise at least one and in particular all of the following further oxides of pentavalent elements $Me^V{}_2O_5$ in the specified amounts:

| Component | wt.-% |
| --- | --- |
| $P_2O_5$ | 0 to 5.0 |
| $V_2O_5$ | 0 to 6.0 |
| $Ta_2O_5$ | 0 to 5.0 |
| $Nb_2O_5$ | 0 to 5.0. |

In addition, the glass and the glass ceramic can comprise 0 to 6.0 wt.-% oxide of hexavalent elements $Me^{VI}O_3$, wherein this $Me^{VI}O_3$ is selected in particular from $WO_3$ and/or $MoO_3$. Particularly preferably, the glass and the glass ceramic comprise at least one and in particular all of the following oxides $Me^{VI}O_3$ in the specified amounts:

| Component | wt.-% |
| --- | --- |
| $WO_3$ | 0 to 6.0 |
| $MoO_3$ | 0 to 5.0. |

Furthermore, the glass and the glass ceramic can comprise oxides of further f elements, such as oxides of Pr, Nd, Gd, Dy, Er and Yb and in particular oxides of Er.

Furthermore, the glass and the glass ceramic can comprise 0 to 5.0 and in particular 0 to 2.0 wt.-% fluorine.

A glass and a glass ceramic which comprise at least one and preferably all of the following components in the specified amounts are particularly preferred:

| Component | wt.-% |
| --- | --- |
| $SiO_2$ | 46.0 to 77.0 |
| $Al_2O_3$ | 0.3 to 39.0 |
| Cerium, calculated as $CeO_2$ | 0.7 to 7.5 |
| Tin, calculated as SnO | 0.2 to 3.0 |
| Terbium, calculated as $Tb_4O_7$ | 0 to 2.0 |
| $Li_2O$ | 0 to 18.0 |
| $Me^I{}_2O$ | 0 to 13.0 |
| $Me^{II}O$ | 0 to 22.0 |
| $Me^{III}{}_2O_3$ | 0 to 10.0 |
| $Me^{IV}O_2$ | 0 to 10.0 |
| $Me^V{}_2O_5$ | 0 to 8.0 |
| $Me^{VI}O_3$ | 0 to 6.0 |
| Fluorine | 0 to 5.0, | wherein $Me^I{}_2O$, $Me^{II}O$, $Me^{III}{}_2O_3$, $Me^{IV}O_2$, $Me^V{}_2O_5$ and $Me^{VI}O_3$ in particular have the meanings specified above.

In a further particularly preferred embodiment, the glass and the glass ceramic comprise at least one and preferably all of the following components:

| Component | wt.-% |
| --- | --- |
| $SiO_2$ | 46.0 to 77.0 |
| $Al_2O_3$ | 0.3 to 39.0 |
| Cerium, calculated as $CeO_2$ | 0.7 to 7.5 |
| Tin, calculated as SnO | 0.2 to 3.0 |
| Terbium, calculated as $Tb_4O_7$ | 0 to 2.0 |
| $Li_2O$ | 0 to 18.0 |
| $Na_2O$ | 0 to 8.0 |
| $K_2O$ | 0 to 5.0 |
| $Rb_2O$ | 0 to 7.0 |
| $Cs_2O$ | 0 to 13.0 |
| MgO | 0 to 13.0 |
| CaO | 0 to 4.0 |
| SrO | 0 to 3.0 |
| ZnO | 0 to 4.0 |
| BaO | 0 to 10.0 |
| $B_2O_3$ | 0 to 5.0 |
| $Y_2O_3$ | 0 to 3.0 |
| $La_2O_3$ | 0 to 2.0 |
| $Ga_2O_3$ | 0 to 2.0 |
| $In_2O_3$ | 0 to 1.0 |
| $ZrO_2$ | 0 to 8.0 |
| $GeO_2$ | 0 to 5.0 |
| $TiO_2$ | 0 to 5.0 |
| $P_2O_5$ | 0 to 5.0 |
| $V_2O_5$ | 0 to 6.0 |
| $Ta_2O_5$ | 0 to 5.0 |
| $Nb_2O_5$ | 0 to 5.0 |
| $WO_3$ | 0 to 6.0 |
| $MoO_3$ | 0 to 5.0 |
| $Er_2O_3$ | 0 to 1.0 |
| Fluorine | 0 to 5.0. |

The invention likewise relates to precursors with a corresponding composition from which the glass ceramic according to the invention can be produced by heat treatment. These precursors are a glass with a corresponding composition (also referred to as starting glass) and a glass with a corresponding composition with nuclei. The term "corresponding composition" means that these precursors comprise the same components in the same amounts as the glass ceramic, wherein the components with the exception of fluorine are calculated as oxides, as is customary in the case of glasses and glass ceramics.

The invention likewise relates to a glass according to the invention which comprises nuclei for the crystallization. Through heat treatment of the glass according to the invention, the glass with nuclei according to the invention can first be produced, which in turn can be converted through further heat treatment into the glass ceramic according to the invention.

The invention also relates to a process for the preparation of the glass according to the invention or the glass ceramic according to the invention, in which process tin is used in divalent form and in particular as SnO.

The glass according to the invention is produced in particular in such a way that a mixture of suitable starting materials, such as carbonates, oxides, phosphates and fluorides, is melted at temperatures of in particular from 1500 to 1800° C., for 0.5 to 10 h. In order to achieve a particularly high homogeneity, the glass melt obtained can be poured into water in order to form a glass granulate, and the granulate obtained can then be melted again.

The melt can then be poured into moulds, e.g. steel or graphite moulds, in order to produce blanks of the glass, so-called solid glass blanks or monolithic blanks. Usually, these monolithic blanks are first relaxed, e.g. by being kept at 450 to 600° C. for 5 to 120 min.

It is likewise possible to place the melt in water again in order to produce a granulate. This granulate can then be pressed, after grinding and optionally addition of further components, to form a blank, a so-called powder compact. The glass can finally also be processed to form a powder after granulation.

The glass with nuclei can then be produced from the glass by heat treatment. This is also referred to as the nucleation process. The invention is therefore likewise directed to a process for the preparation of the glass with nuclei, in which the glass is subjected to a heat treatment at a temperature of from 450 to 600° C. and in particular 500 to 550° C. for a duration of in particular from 5 to 120 min and preferably 10 to 60 min.

The glass ceramic according to the invention can be formed from the glass with nuclei by heat treatment. The invention is therefore likewise directed to a process for the preparation of the glass ceramic according to the invention, in which the glass, in particular the glass with nuclei, is subjected to at least one heat treatment at a temperature of from 700 to 950° C. for a duration of in particular 5 to 120 min and preferably 10 to 60 min.

The glass according to the invention or the glass with nuclei according to the invention can be subjected to the at least one heat treatment e.g. in the form of a monolithic glass blank or a powder compact.

The at least one heat treatment carried out in the process according to the invention can also be effected within the during a hot pressing, in particular of a monolithic glass blank, or during a sintering-on, in particular of a powder.

Thus, in a preferred embodiment, the invention relates to a process for the preparation of the glass ceramic according to the invention, in which
(a) powder of the glass according to the invention, optionally after the addition of further components, such as other glasses, glass ceramics and/or pressing agents, is pressed to form a powder compact, and
(b) the powder compact is subjected to a heat treatment at a temperature of from 700 to 950° C., for a duration of in particular from 5 to 120 min.

In a further preferred embodiment, the invention relates to a process for the preparation of the glass ceramic according to the invention, in which
(a') melt of the glass is shaped to form a glass blank, in particular by pouring into a mould, and
(b') the glass blank is subjected to a heat treatment at a temperature of from 700 to 900° C. for a duration of in particular from 5 to 120 min.

In both preferred embodiments of the process according to the invention, a nucleation can optionally be carried out before the heat treatment in step (b) or (b').

The invention further relates to a glass according to the invention and a glass ceramic according to the invention, which have a whiteish-blue fluorescence in the CIE colour space.

The glasses and glass ceramics with cerium and tin content according to the invention are, in particular, suitable as blending components for setting the fluorescence properties of other glasses and glass ceramics. A glass or a glass ceramic comprising the glass with cerium and tin content according to the invention or the glass ceramic with cerium and tin content according to the invention, therefore represent a further subject of the invention. A glass and a glass ceramic are particularly preferred, which comprise the glass with cerium and tin content according to the invention or the glass ceramic with cerium and tin content according to the invention in an amount of from 0.1 to 50 wt.-%, in particular 0.2 to 40 wt.-%, preferably 0.5 to 30 wt.-%, particularly preferably 1 to 20 wt.-% and more preferably 5 to 10 wt.-%.

The glass according to the invention or the glass ceramic according to the invention with a cerium and tin content can in particular be used as component of an inorganic-inorganic composite or in combination with a variety of other glasses and/or glass ceramics, wherein the composites or combinations can in particular be used as dental materials. Particularly preferably, the composites or combinations can be present in the form of sintered blanks. Examples of other glasses and glass ceramics for the production of inorganic-inorganic composites and of combinations are disclosed in DE 43 14 817 A1, DE 44 23 793 C1, DE 44 23 794 C1, DE 44 28 839 A1, DE 196 47 739 A1, DE 197 25 552 A1, DE 100 31 431 A1, EP 0 827 941 A1, EP 0 916 625 A1, WO 00/34196 A2, EP 1 505 041 A1, EP 1 688 398 A1, EP 2 287 122 A1, EP 2 377 831 A1, EP 2 407 439 A1, WO 2013/053863 A2, WO 2013/053864 A2, WO 2013/053865 A2, WO 2013/053866 A2, WO 2013/053867 A2, WO 2013/053868 A2, WO 2013/164256 A1, WO 2014/170168 A1, WO 2014/170170 A2, WO 2015/067643 A1, WO 2015/155038 A1, WO 2015/173394 A1, WO 2016/120146 A1, WO 2017/032745 A1 and WO 2017/055010 A1. These glasses and glass ceramics belong to the silicate, borate, phosphate or aluminosilicate group. Preferred glasses and glass ceramics are of the $SiO_2$—$Al_2O_3$—$K_2O$ type (with cubic or tetragonal leucite crystals), $SiO_2$—$B_2O_3$-$Na_2$a type, alkali-silicate type, alkali-zinc-silicate type, silico-phosphate type and/or $SiO_2$—$ZrO_2$ type. Particularly preferred are lithium silicate glass ceramics and in particular glass ceramics which comprise lithium metasilicate or lithium disilicate as main crystal phase and optionally further crystal phases such as apatite, diopside, quartz and/or wollastonite, as well as glass ceramics which comprise $SiO_2$, in particular in the form of low quartz, as main crystal phase. The fluorescence properties can in particular be set as desired by mixing such glasses or glass ceramics with the glasses and/or glass ceramics with cerium and tin content according to the invention.

The glass ceramics according to the invention and the glasses according to the invention, in particular in the form of composites and combinations, are present in particular in the form of powders, granulates or blanks in any shape and size, e.g. monolithic blanks, such as platelets, cuboids or cylinders, or powder compacts, in unsintered, partially sintered or densely sintered form. In these forms, they can easily be further processed, e.g. to form dental restorations. However, they can also be present in the form of dental restorations such as inlays, onlays, crowns, partial crowns, bridges, veneers, facets or abutments.

Dental restorations such as inlays, onlays, crowns, partial crowns, bridges, veneers, facets or abutments can be produced from the glass ceramics according to the invention and the glasses according to the invention, in particular in the form of composites and combinations. The invention therefore relates to the use thereof as dental material and in particular the use thereof for the preparation of dental restorations. It is preferred that the glass ceramic or the glass is given the shape of the desired dental restoration by pressing or machining.

The pressing is usually effected under increased pressure and at increased temperature. It is preferred that the pressing is effected at a temperature of from 700 to 1150° C. and in particular 700 to 1000° C. It is further preferred to carry out the pressing at a pressure of from 10 to 30 bar. During pressing, the desired shape change is achieved by viscous flow of the material used. The glass according to the invention and the glass with nuclei according to the invention as well as preferably the glass ceramic according to the invention can be used for the pressing. The glasses and glass ceramics according to the invention can be used in particular in the form of blanks in any shape and size, e.g. monolithic blanks or powder compacts, e.g. in unsintered, partially sintered or densely sintered form.

The machining is usually effected by material-removal processes and in particular by milling and/or grinding. It is particularly preferred that the machining is carried out in a CAD/CAM process. The glass according to the invention, the glass with nuclei according to the invention as well as the glass ceramic according to the invention can be used for the machining. The glasses and glass ceramics according to the invention can be used in particular in the form of blanks, e.g. monolithic blanks or powder compacts, e.g. in unsintered, partially sintered or densely sintered form. The glass ceramic according to the invention is preferably used for the machining. The glass ceramic according to the invention can also be used in a not completely crystallized form which has been produced by heat treatment at a lower temperature. This offers the advantage that easier machining and thus the use of simpler apparatus for machining are possible. After the machining of such a partially crystallized material, the latter is regularly subjected to a further heat treatment in order to bring about a further crystallization.

The glass ceramics according to the invention and the glasses according to the invention, in particular in the form of composites and combinations, are however also suitable as coating material for e.g. ceramics, glass ceramics and metals. The invention is therefore likewise directed to the use of the glasses according to the invention or the glass ceramics according to the invention for coating in particular ceramics, glass ceramics and metals.

The invention also relates to a process for coating ceramics, glass ceramics and metals, in which glass ceramic according to the invention or glass according to the invention, in particular in the form of composites and combinations, is applied to the ceramic, the glass ceramic or the metal and exposed to a temperature of at least 600° C.

This can be effected in particular by sintering-on and preferably by pressing-on. In the case of sintering-on, the glass ceramic or the glass is applied in the usual way, e.g. as powder, to the material to be coated, such as ceramic, glass ceramic or metal, and then sintered. In the case of the preferred pressing-on, glass ceramic according to the invention or glass according to the invention is pressed on, e.g. in the form of powder compacts or monolithic blanks, at an increased temperature of e.g. from 700 to 1150° C. and in particular 700 to 1000° C., with application of pressure, e.g. 10 to 30 bar. For this, the methods described in EP 231 773 and the press furnace disclosed there can in particular be used. Suitable commercial furnaces are the Programat-type furnaces from Ivoclar Vivadent A G, Liechtenstein.

Because of the above-described properties of the glass ceramics according to the invention and the glasses according to the invention, these are suitable in particular for use in dentistry. A subject of the invention is therefore also the use of the glass ceramics according to the invention or the glasses according to the invention, in particular in the form of composites and combinations, as dental material and in particular for the preparation of dental restorations or as coating material for dental restorations, such as crowns, bridges and abutments.

The invention therefore also relates to a process for the preparation of a dental restoration, in particular an inlay, onlay, crown, partial crown, bridge, veneer, facet or abutment, in which the glass ceramic according to the invention or the glass according to the invention, in particular in the form of composites and combinations, is given the shape of the desired dental restoration by pressing, sintering or machining, in particular in a CAD/CAM process.

The invention is described in further detail in the following with reference to non-limitative examples.

EXAMPLES

A total of 18 glasses according to the invention were produced with the compositions specified in Table I, wherein the oxidation states of the specified oxides relate to the oxidation states of the raw materials used. The glasses were crystallized to form glass ceramics according to Table II. Herein,

| | |
|---|---|
| $T_g$ | denotes glass transition temperature, determined by means of DSC |
| $T_S$ and $t_S$ | denote temperature and time used for melting |
| $T_N$ and $t_N$ | denote temperature and time used for nucleation |
| $T_C$ and $t_c$ | denote temperature and time used for crystallization |
| $T_{Sinter}$ and $t_{Sinter}$ | denote temperature and time used for sintering. |

In the examples, starting glasses with the compositions specified in Table I were first melted on a scale of from 100 to 200 g from usual raw materials at the temperature $T_s$ for a duration $t_s$. Glass frits were produced by pouring the molten starting glasses into water. The four method variants A) to D) specified below were used for the further processing of the glass frits:

A) Preparation of Sintered Powder Compacts

In Examples 1 to 3 (according to the invention) and 4 (comparison) the fluorescence of the glass frits obtained was determined visually under a UV lamp. All the glass frits exhibited a fluorescence.

Thereafter, the glass frits obtained were ground to a grain size of <112 µm in a zirconium oxide mill. About 4 g of these powders were pressed to form cylindrical blanks and subjected to a heat treatment at the temperature $T_N$ for a duration $t_N$, whereby nucleation could take place. The blanks were then sintered under vacuum in a sintering furnace (Programat® from Ivoclar Vivadent AG) at a temperature $T_{sinter}$ and for a holding time of $t_{sinter}$ to form dense glass ceramic bodies. The fluorescence of the glass ceramic bodies thus obtained was determined visually under a UV lamp. All the bodies exhibited a fluorescence.

The examples were repeated, wherein the sintering was effected in air. While in the case of Examples 1 to 3 according to the invention a fluorescence was obtained that was only slightly reduced compared with the sintering under vacuum, in the case of comparison example 4 (no tin) no appreciable fluorescence was observed.

B) Monolithic Glass Blocks

In Examples 5 to 15 (according to the invention) and 16 (comparison) the glass frits obtained were again melted at the temperature $T_s$ for a duration $t_s$. The melts of the starting glass obtained were then poured into a graphite mould in order to produce monolithic glass blocks. After that, the glass monoliths were relaxed at the temperature $T_N$ for a duration $t_N$, whereby nucleation could take place. The fluorescence of the glass monoliths was then determined visually under a UV lamp. All the glass monoliths, with the exception of comparison example 16 (no tin), exhibited a fluorescence.

In Examples 6 to 15 (according to the invention) and 16 (comparison) the glass monoliths were then heated to a temperature $T_c$ for a duration $t_c$ in order to form glass ceramics. The fluorescence of the glass ceramics obtained was in turn determined visually under a UV lamp. All the glass ceramics, with the exception of comparison example 16 (no tin), exhibited a fluorescence.

C) Glass Frits

In Examples 17 to 19 the fluorescence of the glass frits obtained was determined visually under a UV lamp. All the glass frits exhibited a fluorescence.

D) Glass According to the Invention as Blending Components

A glass frit obtained according to Example 20 was ground and added to a ground glass powder with a composition according to WO 2015/173394 A1, in different amounts (5, 10, 20 and 30 wt.-% relative to the mixture). In each case about 4 g of these mixtures were then pressed to form cylindrical blanks and sintered in a sintering furnace (Programat® from Ivoclar Vivadent AG) at a temperature of 860° C. for a holding time of 60 min to form dense glass ceramic bodies. The fluorescence was then determined visually under a UV lamp. All the bodies exhibited a fluorescence.

TABLE I

| Composition | 1 wt.-% | 2 wt.-% | 3 wt.-% | 4** wt.-% | 5 wt.-% | 6 wt.-% | 7 wt.-% | 8 wt.-% | 9 wt.-% | 10 wt.-% |
|---|---|---|---|---|---|---|---|---|---|---|
| $SiO_2$ | 73.8 | 73.4 | 70.8 | 73.3 | 63.7 | 73.2 | 73.2 | 73.4 | 73.8 | 76.2 |
| $Al_2O_3$ | 2.6 | 2.6 | 2.5 | 2.6 | 5.4 | 0.5 | 2.6 | 2.6 | 2.6 | 2.7 |
| $CeO_2$ | 1.3 | 1.8 | 0.9 | — | 7.3 | 4.4 | 1.8 | 1.8 | 1.8 | 0.9 |
| $Ce_2O_3$* | — | — | — | 2.4 | — | — | — | — | — | — |
| SnO | 0.5 | 0.5 | 0.3 | — | 2.8 | 1.4 | 0.5 | 0.5 | 0.5 | 0.2 |
| $Li_2O$ | 9.0 | 8.9 | 7.9 | 8.9 | 15.8 | 7.9 | 8.9 | 8.9 | 8.6 | 8.9 |
| $Na_2O$ | — | — | — | — | — | — | — | — | — | — |
| $K_2O$ | 3.2 | 3.2 | 3.4 | 3.2 | 5.0 | 3.5 | 3.2 | 3.2 | 3.2 | 3.3 |
| MgO | 2.4 | 2.4 | 1.7 | 2.4 | — | 1.7 | 2.4 | 2.4 | 2.7 | 2.8 |
| CaO | — | — | 3.0 | — | — | 3.0 | — | — | — | — |
| SrO | — | — | — | — | — | — | — | — | — | — |
| ZnO | 3.5 | 3.5 | — | 3.5 | — | — | 3.5 | 3.5 | 0.7 | 0.7 |
| $B_2O_3$ | — | — | — | — | — | — | — | — | 0.6 | 0.6 |
| $Y_2O_3$ | — | — | — | — | — | — | — | — | — | — |
| $La_2O_3$ | — | — | — | — | — | — | — | — | — | — |
| $GeO_2$ | — | — | 1.4 | — | — | — | — | — | — | — |
| $ZrO_2$ | — | — | 1.0 | — | — | — | — | — | — | — |
| $P_2O_5$ | 3.3 | 3.3 | 3.4 | 3.3 | — | 3.6 | 3.3 | 3.3 | 3.2 | 3.3 |
| $V_2O_5$ | — | — | — | — | — | — | 0.1 | — | — | — |
| $Ta_2O_5$ | — | — | 3.7 | — | — | — | — | — | 1.9 | — |
| $Er_2O_3$ | — | — | — | — | — | — | 0.1 | — | — | — |
| $Tb_4O_7$ | 0.4 | 0.4 | — | 0.4 | — | 0.8 | 0.4 | 0.4 | 0.4 | 0.4 |
| F | — | — | — | — | — | — | — | — | — | — |
| Σ | 100.0 | 100.0 | 100.0 | 100.0 | 100.0 | 100.0 | 100.0 | 100.0 | 100.0 | 100.0 |

| Composition | 11 wt.-% | 12 wt.-% | 13 wt.-% | 14 wt.-% | 15 wt.-% | 16** wt.-% | 17 wt.-% | 18 wt.-% | 19 wt.-% | 20 wt.-% |
|---|---|---|---|---|---|---|---|---|---|---|
| $SiO_2$ | 74.1 | 73.8 | 73.8 | 71.8 | 70.8 | 76.5 | 64.6 | 46.8 | 63.9 | 73.9 |
| $Al_2O_3$ | 2.6 | 2.6 | 2.6 | 2.6 | 2.5 | 2.7 | 4.0 | 38.8 | 5.0 | 0.5 |
| $CeO_2$ | 1.8 | 1.8 | 1.8 | 4.4 | 0.9 | 0.9 | 1.9 | 1.5 | 1.7 | 4.4 |
| $Ce_2O_3$* | — | — | — | — | — | — | — | — | — | — |
| SnO | 0.5 | 0.5 | 0.5 | 0.5 | 0.3 | — | 0.7 | 0.6 | 0.7 | 1.4 |
| $Li_2O$ | 8.7 | 8.6 | 8.9 | 8.7 | 7.9 | 9.2 | 16.0 | — | 3.2 | 8.0 |
| $Na_2O$ | — | — | — | — | — | — | — | — | 7.4 | — |
| $K_2O$ | 3.2 | 3.2 | 3.2 | 3.1 | 3.4 | 3.3 | 3.8 | — | 4.6 | 3.5 |
| MgO | 2.7 | 2.7 | 2.4 | 2.3 | 1.7 | 3.0 | 1.8 | 12.3 | 0.5 | 1.7 |
| CaO | — | — | — | — | 3.0 | — | 3.3 | — | 1.8 | 3.0 |
| SrO | — | — | — | — | — | — | — | — | 2.4 | — |
| ZnO | 0.7 | 0.7 | 3.5 | 3.4 | — | 0.7 | — | — | 3.5 | — |
| $B_2O_3$ | 0.6 | 0.6 | — | — | — | — | — | — | 4.0 | — |
| $Y_2O_3$ | — | 1.9 | — | — | — | — | — | — | — | — |
| $La_2O_3$ | 1.4 | — | — | — | — | — | — | — | — | — |
| $GeO_2$ | — | — | — | — | 1.4 | — | — | — | — | — |
| $ZrO_2$ | — | — | — | — | 1.0 | — | — | — | — | — |
| $P_2O_5$ | 3.3 | 3.2 | 3.3 | 3.2 | 3.4 | 3.3 | 3.9 | — | — | 3.6 |
| $V_2O_5$ | — | — | — | — | — | — | — | — | — | — |
| $Ta_2O_5$ | — | — | — | — | 3.7 | — | — | — | — | — |
| $Er_2O_3$ | — | — | — | — | — | — | — | — | — | — |
| $Tb_4O_7$ | 0.4 | 0.4 | — | — | — | 0.4 | — | — | — | — |
| F | — | — | — | — | — | — | — | — | 1.3 | — |
| Σ | 100.0 | 100.0 | 100.0 | 100.0 | 100.0 | 100.0 | 100.0 | 100.0 | 100.0 | 100.0 |

*Used as cerium(III) acetylacetonate;
**comparison

TABLE II

| | Example | | | | | | | | | |
|---|---|---|---|---|---|---|---|---|---|---|
| | 1 | 2 | 3 | 4** | 5 | 6 | 7 | 8 | 9 | 10 |
| $T_g$ [° C.] | | | | | 469 | 488 | | | | |
| $T_S$ [° C.] | 1600 | 1600 | 1600 | 1600 | 1650 | 1650 | 1600 | 1600 | 1600 | 1600 |
| $t_S$ [min] | 120 | 120 + 120 | 60 | 120 | 240 | 60 | 120 + 120 | 120 + 120 | 120 + 120 | 120 |
| $T_N$ [° C.] | 500 | 500 | 500 | 500 | 490 | 520 | 500 | 500 | 500 | 500 |
| $T_N$ [min] | 60 | 20 | 20 | 60 | 120 | 10 | 60 | 60 | 60 | 60 |
| $T_C$ [° C.] | — | — | — | — | — | 850 | 820 | 820 | 820 | 820 |
| $t_C$ [min] | — | — | — | — | — | 10 | 30 | 30 | 30 | 30 |
| $T_{Sinter}$ [° C.] | 860 | 860 | 860 | 860 | — | — | — | — | — | — |
| $t_{Sinter}$ [min] | 30 | 60 | 60 | 30 | — | — | — | — | — | — |
| Fluorescence glass | blue | strong blue | blue-white | blue | blue | blue-white | blue | strong blue | blue | blue |
| Fluorescence glass ceramic | blue | blue | blue-white | blue | | blue-white | blue | strong blue | blue | blue |

| | Example | | | | | | | | |
|---|---|---|---|---|---|---|---|---|---|
| | 11 | 12 | 13 | 14 | 15 | 16** | 17 | 18 | 19 |
| $T_g$ [° C.] | | | | | | | 435 | 802 | 445 |
| $T_S$ [° C.] | 1600 | 1600 | 1600 | 1600 | 1600 | 1600 | 1600 | 1600 | 1600 |
| $t_S$ [min] | 120 | 120 | 120 + 120 | 120 + 120 | 60 | 120 | 120 | 60 | 60 |
| $T_N$ [° C.] | 500 | 500 | 490 | 500 | 500 | 500 | — | — | — |
| $T_N$ [min] | 60 | 60 | 10 | 10 | 10 | 60 | — | — | — |
| $T_C$ [° C.] | 820 | 820 | 820 | 820 | 810 | 820 | — | — | — |
| $t_C$ [min] | 30 | 30 | 30 | 30 | 60 | 30 | — | — | — |
| $T_{Sinter}$ [° C.] | — | — | — | — | — | — | — | — | — |
| $t_{Sinter}$ [min] | — | — | — | — | — | — | — | — | — |
| Fluorescence glass | blue | blue | strong blue | strong blue | blue-white | none | blue | blue | blue |
| Fluorescence glass ceramic | blue | blue | strong blue | pale blue | blue-white | none | | | |

**comparison

The invention claimed is:

1. Glass ceramic with cerium and tin content, which comprises the following components:

| Component | wt.-% |
|---|---|
| $SiO_2$ | 42.0 to 80.0 |
| $Al_2O_3$ | 0.1 to 42.0 |
| Cerium, calculated as $CeO_2$ | 0.5 to 10.0 |
| Tin, calculated as SnO | 0.1 to 4.0 | wherein the molar ratio of cerium, calculated as $CeO_2$, to tin, calculated as SnO, lies in the range of from 10:1 to more than 1:1.

2. Glass ceramic according to claim 1, which comprises 46.0 to 77.0 wt.-% $SiO_2$.

3. Glass ceramic according to claim 1, which comprises 0.3 to 39.0 wt.-% $Al_2O_3$.

4. Glass ceramic according to claim 1, which comprises 0.7 to 7.5 wt.-% cerium, calculated as $CeO_2$.

5. Glass ceramic according to claim 1, which comprises 0.2 to 3.0 wt.-% tin, calculated as SnO.

6. Glass ceramic according to claim 1, in which the molar ratio of cerium, calculated as $CeO_2$, to tin, calculated as SnO, lies in the range of from 10:1 to 2:1.

7. Glass ceramic according to claim 1, which comprises 0 to 2.0 wt.-% terbium, calculated as $Tb_4O_7$.

8. Glass ceramic according to claim 1, which comprises 0 to 18.0 wt.-% $Li_2O$.

9. Glass ceramic according to claim 1, which comprises 0 to 10.0 wt.-% BaO.

10. Glass ceramic according to claim 1, which comprises at least one of the following components in the specified amounts:

| Component | wt.-% |
|---|---|
| $SiO_2$ | 46.0 to 77.0 |
| $Al_2O_3$ | 0.3 to 39.0 |
| Cerium, calculated as $CeO_2$ | 0.7 to 7.5 |
| Tin, calculated as SnO | 0.2 to 3.0 |
| Terbium, calculated as $Tb_4O_7$ | 0 to 2.0 |
| $Li_2O$ | 0 to 18.0 |
| $Me^I_2O$ | 0 to 13.0 |
| $Me^{II}O$ | 0 to 22.0 |
| $Me^{III}_2O_3$ | 0 to 10.0 |
| $Me^{IV}O_2$ | 0 to 10.0 |
| $Me^V_2O_5$ | 0 to 8.0 |
| $Me^{VI}O_3$ | 0 to 6.0 |
| Fluorine | 0 to 5.0, | wherein
$Me^I_2O$ is selected from $Na_2O$, $K_2O$, $Rb_2O$ and/or $Cs_2O$,
$Me^{II}O$ is selected from MgO, CaO, SrO and/or ZnO,
$Me^{III}_2O_3$ is selected from $B_2O_3$, $Y_2O_3$, $La_2O_3$, $Ga_2O_3$ and/or $In_2O_3$,
$Me^{IV}O_2$ is selected from $ZrO_2$ and/or $GeO_2$,
$Me^V_2O_5$ is selected from $P_2O_5$, $V_2O_5$, $Ta_2O_5$ and/or $Nb_2O_5$ and
$Me^{VI}O_3$ is selected from $WO_3$ and/or $MoO_3$.

11. Glass ceramic material, which comprises the glass ceramic with cerium and tin content as defined in claim 1.

12. Glass ceramic according to claim 1, wherein the glass ceramic is present in the form of a powder, a granulate, a blank or a dental restoration.

13. A process of producing the glass ceramic according to claim 1 which process comprises melting suitable starting material, wherein the tin is used at least partially in divalent form.

14. Process for the preparation of the glass ceramic according to claim 1, in which a glass which comprises the following components:

| Component | wt.-% |
|---|---|
| $SiO_2$ | 42.0 to 80.0 |
| $Al_2O_3$ | 0.1 to 42.0 |
| $B_2O_3$ | 0 to 5.0 |
| Cerium, calculated as $CeO_2$ | 0.5 to 10.0 |
| Tin, calculated as SnO | 0.1 to 4.0 | wherein the molar ratio of cerium, calculated as $CeO_2$, to tin, calculated as SnO, lies in the range of from 10:1 to more than 1:1,
is subjected to at least one heat treatment at a temperature of from 700 to 950° C.

15. Process according to claim 14, in which
(a) powder of the glass, optionally after the addition of further components, is pressed to form a powder compact, and
(b) the powder compact is subjected to a heat treatment at a temperature of from 700 to 950° C.,
or
(a') melt of the glass is shaped to form a glass blank, and
(b') the glass blank is subjected to a heat treatment at a temperature of from 700 to 900° C.

16. Process for setting the fluorescence of a glass or of a glass ceramic, which process comprises using the glass ceramic according to claim 1 as blending component.

17. The glass ceramic according to claim 1, wherein the glass ceramic is used as a dental material.

18. Process for the preparation of a dental restoration, which process comprises giving the glass ceramic according to claim 1 the shape of the desired dental restoration by pressing, sintering or machining.

* * * * *